(12) United States Patent
Takeshima

(10) Patent No.: US 10,610,187 B2
(45) Date of Patent: Apr. 7, 2020

(54) RADIOGRAPHIC IMAGING APPARATUS, CONTROL APPARATUS, RADIOGRAPHIC IMAGING SYSTEM, METHOD OF CONTROLLING RADIOGRAPHIC IMAGING SYSTEM

(71) Applicant: CANON KABUSHIKI KAISHA, Tokyo (JP)

(72) Inventor: Mina Takeshima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 143 days.

(21) Appl. No.: 15/778,107

(22) PCT Filed: Nov. 10, 2016

(86) PCT No.: PCT/JP2016/004856
§ 371 (c)(1),
(2) Date: May 22, 2018

(87) PCT Pub. No.: WO2017/090237
PCT Pub. Date: Jun. 1, 2017

(65) Prior Publication Data
US 2018/0353150 A1     Dec. 13, 2018

(30) Foreign Application Priority Data

Nov. 28, 2015  (JP) ................................ 2015-232522

(51) Int. Cl.
*A61B 6/00* (2006.01)
*G01T 1/185* (2006.01)

(52) U.S. Cl.
CPC ............ *A61B 6/542* (2013.01); *A61B 6/4283* (2013.01); *A61B 6/54* (2013.01); *A61B 6/56* (2013.01);
(Continued)

(58) Field of Classification Search
CPC ......... G01T 1/185; A61B 6/4283; A61B 6/54; A61B 6/542; A61B 6/56; A61B 6/563; A61B 6/566
See application file for complete search history.

(56) References Cited

U.S. PATENT DOCUMENTS

| 2009/0046828 A1* | 2/2009 | Ohta | A61B 6/00 378/1 |
|---|---|---|---|
| 2011/0188633 A1* | 8/2011 | Ohta | H05G 1/10 378/102 |

(Continued)

FOREIGN PATENT DOCUMENTS

JP     2013162963 A     8/2013

OTHER PUBLICATIONS

International Search Report and Written Opinion of the International Searching Authority for PCT/JP2016/004856, Feb. 2017.

*Primary Examiner* — Marcus H Taningco
(74) *Attorney, Agent, or Firm* — Canon U.S.A., Inc. IP Division

(57) ABSTRACT

A radiographic imaging system includes a radiation detector, a controller, and determining unit. The radiation detector detects radiation emitted from a radiation source. The controller is capable of selectively performing wired communication or wireless communication with the radiation detector and controls the radiation detector and the radiation source. The determining unit determines whether or not a delivered dose delivered to the radiation detector reaches a reference value, by using a predetermined determination criterion on the basis of the detection result from the radiation detector. The controller controls the radiation source on the basis of the determination result from the determining unit, and the determining unit switches the predetermined determination criterion in accordance with (Continued)

whether the selected communication is the wireless communication or the wired communication.

15 Claims, 9 Drawing Sheets

(52) U.S. Cl.
CPC .............. *A61B 6/563* (2013.01); *A61B 6/566* (2013.01); *G01T 1/185* (2013.01)

(56) References Cited

U.S. PATENT DOCUMENTS

| | | |
|---|---|---|
| 2011/0249792 A1 | 10/2011 | Lalena |
| 2013/0058456 A1* | 3/2013 | Kuwabara ............ A61B 6/4233 378/62 |
| 2013/0148784 A1 | 6/2013 | Tajima |
| 2013/0195251 A1 | 8/2013 | Saigusa |
| 2013/0208860 A1 | 8/2013 | Sugizaki |
| 2015/0055752 A1 | 2/2015 | Takahashi |

* cited by examiner

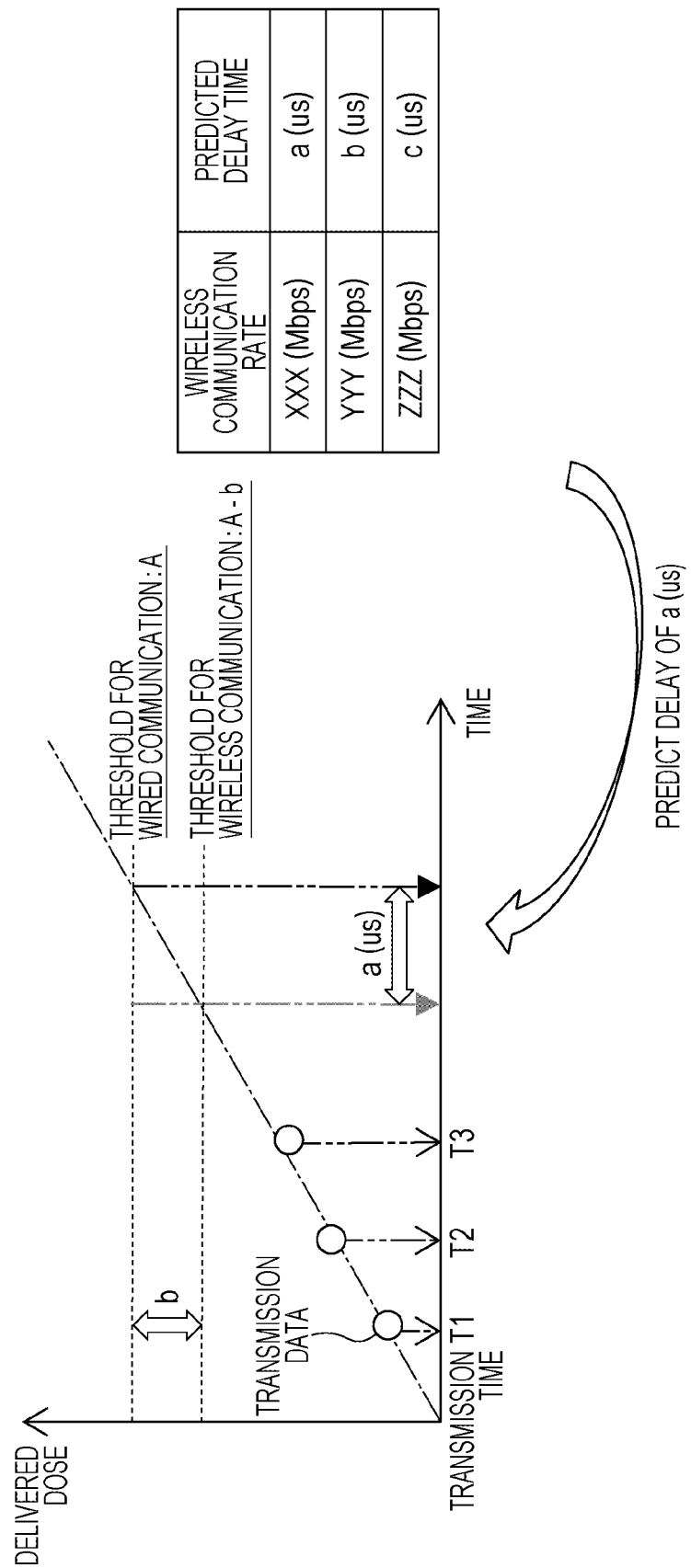

ered. A radiographic imaging apparatus transfers a generated radiographic image to a control apparatus through wired communication or wireless communication.

RADIOGRAPHIC IMAGING APPARATUS, CONTROL APPARATUS, RADIOGRAPHIC IMAGING SYSTEM, METHOD OF CONTROLLING RADIOGRAPHIC IMAGING SYSTEM

TECHNICAL FIELD

The present invention relates to a radiographic imaging apparatus, a control apparatus, a radiographic imaging system, and a method of controlling the radiographic imaging system.

BACKGROUND ART

In medical imaging diagnosis and non-destructive testing using radiation such as X-rays, a radiographic imaging apparatus having a matrix substrate having a pixel array in which a switch such as a thin film transistor (TFT) is combined with a conversion device such as a photoelectric conversion device has become commercially practical. A radiographic imaging apparatus transfers a generated radiographic image to a control apparatus through wired communication or wireless communication.

Recently, expansion of the functionality of a radiographic imaging apparatus has been discussed. As one of the discussions, a radiographic imaging apparatus having a function of monitoring radiation has been discussed. This function enables, for example, detection of a timing at which irradiation of radiation emitted from a radiation source is started, detection of a timing at which irradiation of radiation is to be stopped, and calculation of the dose of irradiation of radiation or the integrated irradiation dose.

PTL 1 discloses a radiographic imaging system including a radiographic imaging apparatus having pixels for monitoring radiation, a radiation source, and a control apparatus. In the radiographic imaging system, when a timing at which irradiation is to be stopped is detected, an irradiation stop signal is transmitted from the radiographic imaging apparatus to the control apparatus through wireless communication.

However, in PTL 1, the radiographic imaging apparatus transmits an irradiation stop signal through wireless communication. Compared with wired communication, the communication speed of wireless communication is slower, the communication is likely to be affected by noise, and communication accuracy is unstable. Therefore, in accordance with the operating environment and communication environment, irradiation may fail to be stopped at a timing at which an adequate dose of irradiation is obtained. Therefore, according to an aspect of the present invention, an advantageous technique for adequately controlling irradiation of radiation in accordance with a communication path is provided in a radiographic imaging system.

CITATION LIST

Patent Literature

PTL 1: Japanese Patent Laid-Open No. 2013-162963

SUMMARY OF INVENTION

Solution to Problem

A radiographic imaging system includes a radiation detector, a controller, and determining unit. The radiation detector detects radiation emitted from a radiation source. The controller is capable of selectively performing wired communication or wireless communication with the radiation detector and controls the radiation detector and the radiation source. The determining unit determines whether or not a delivered dose delivered to the radiation detector reaches a reference value, by using a predetermined determination criterion on the basis of the detection result from the radiation detector. The controller controls the radiation source on the basis of the determination result from the determining unit, and the determining unit switches the predetermined determination criterion in accordance with whether the selected communication is the wireless communication or the wired communication.

Further features of the present invention will become apparent from the following description of exemplary embodiments with reference to the attached drawings.

BRIEF DESCRIPTION OF DRAWINGS

FIG. 6 is a diagram illustrating a process performed by a determining unit according to the first embodiment.

DESCRIPTION OF EMBODIMENTS

First Embodiment

Figure 1:
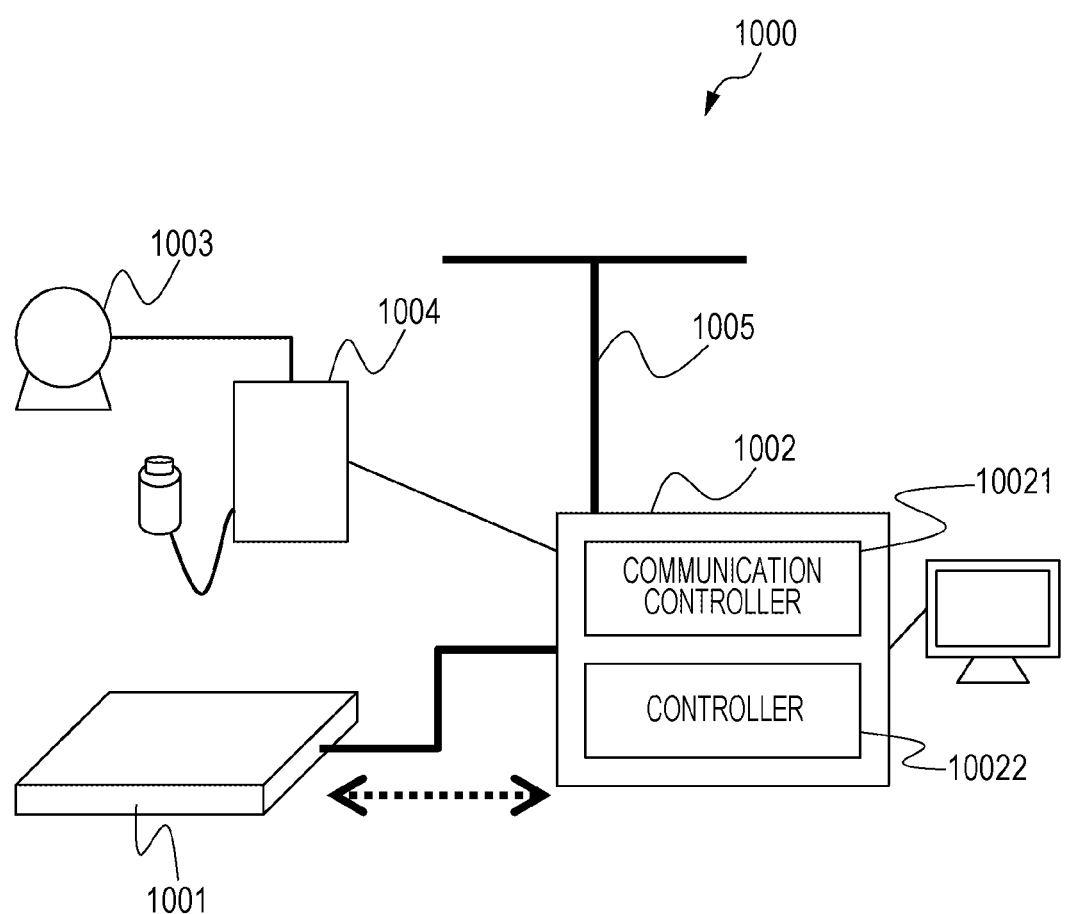
FIG. 1 is a diagram illustrating a radiographic imaging system according to a first embodiment.

Referring to FIG. 1, a radiographic imaging system according to a first embodiment will be described. A radiographic imaging system 1000 is used, for example, in capturing a radiographic image in a hospital. The radiographic imaging system 1000 includes a radiographic imaging apparatus 1001, a control apparatus 1002, a radiation source 1003, and a radiation generating apparatus 1004.

The radiographic imaging apparatus 1001 generates a radiographic image according to radiation emitted from the radiation source 1003 and transmitted through a subject (a patient or a test subject). The radiographic imaging apparatus 1001 transfers the captured radiographic image to the control apparatus 1002. In the first embodiment, the radiographic imaging apparatus 1001 detects a delivered dose of radiation emitted from the radiation source 1003, and determines whether or not irradiation of radiation is to be controlled, by using a predetermined criterion on the basis of the delivered dose obtained through the detection. The radiographic imaging apparatus 1001 may further transmit the determination result to the control apparatus 1002 through wired or wireless communication.

The control apparatus 1002 perform setting of imaging conditions, operational control, and the like on the radiographic imaging apparatus 1001. Further, the control apparatus 1002 controls the radiation generating apparatus 1004 so that radiation emitted from the radiation source 1003 is controlled on the basis of the detection result from the radiographic imaging apparatus 1001 (a radiation detector 100). The control apparatus 1002 includes a communication controller 10021 which communicates with the outside and which transmits various types of information, and a controller 10022 which has overall control of the radiographic imaging system 1000. The communication controller 10021 may communicate with the radiation generating apparatus 1004 and the radiographic imaging apparatus 1001. The communication controller 10021 may communicate with another system via a hospital local-area network (LAN) 1005. The controller 10022 monitors the state of the radiographic imaging apparatus 1001 and that of the radiation generating apparatus 1004 on the basis of information obtained via the communication controller 10021, and controls irradiation of radiation emitted from the radiation source 1003. In the radiographic imaging system 1000, the location of the communication controller 10021 is not limited to this, and the communication controller 10021 may be an apparatus separated from the control apparatus 1002.

The control apparatus 1002 includes various devices for enabling setting of imaging conditions, operational control, and input/output of information such as image information. An input devices is used to receive user operations. Examples of the input device include a character information input device such as a keyboard, a pointing device, such as a mouse or a touch panel, a button, a dial, a joystick, a touch sensor, and a touchpad. An output device is constituted by, for example, a display or a monitor.

The radiation generating apparatus 1004 exerts control so that the radiation source 1003 emits radiation. The radiation generating apparatus 1004 includes an irradiation switch. A user presses the irradiation switch so as to cause the radiation source 1003 to emit radiation. The radiation source 1003 includes, for example, a rotor and a radiation tube in which, in order to generate radiation, electrons are accelerated with a high voltage and the accelerated electrons collide against an anode.

Figure 2:
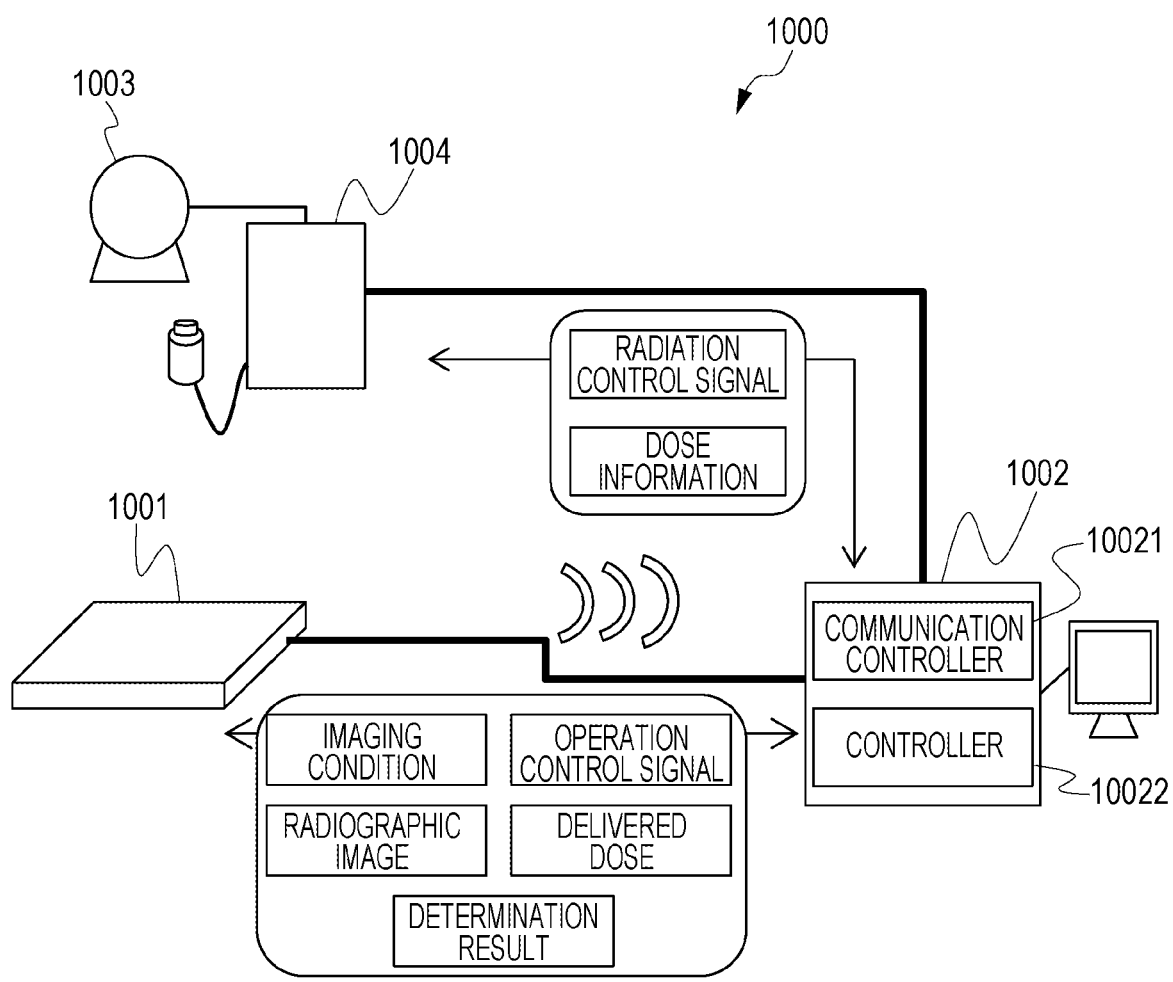
FIG. 2 is a diagram illustrating information received/transmitted by a control apparatus according to the first embodiment.

Referring to FIG. 2, various types of information exchanged in the radiographic imaging system 1000 will be described. FIG. 2 is a diagram illustrating information exchanged between the control apparatus 1002 and the radiographic imaging apparatus 1001 and between the control apparatus 1002 and the radiation generating apparatus 1004.

The control apparatus 1002 exchanges, with the radiographic imaging apparatus 1001, information, such as imaging conditions, an operation control signal, a radiographic image, a delivered dose, and a determination result of dose control. The control apparatus 1002 exchanges dose information, an irradiation control signal, and the like with the radiation generating apparatus 1004.

The dose information indicates a dose of irradiation using the radiation source 1003. The delivered dose indicates a dose of radiation that reaches the radiation detector (100 in FIG. 4). The dose of radiation is a part of the dose of irradiation using the radiation source 1003. The determination result of dose control encompasses, for example, at least two signals, an irradiation stop signal for stopping irradiation using the radiation source 1003 and a continuous irradiation signal for continuing irradiation using the radiation source 1003.

Figure 3:
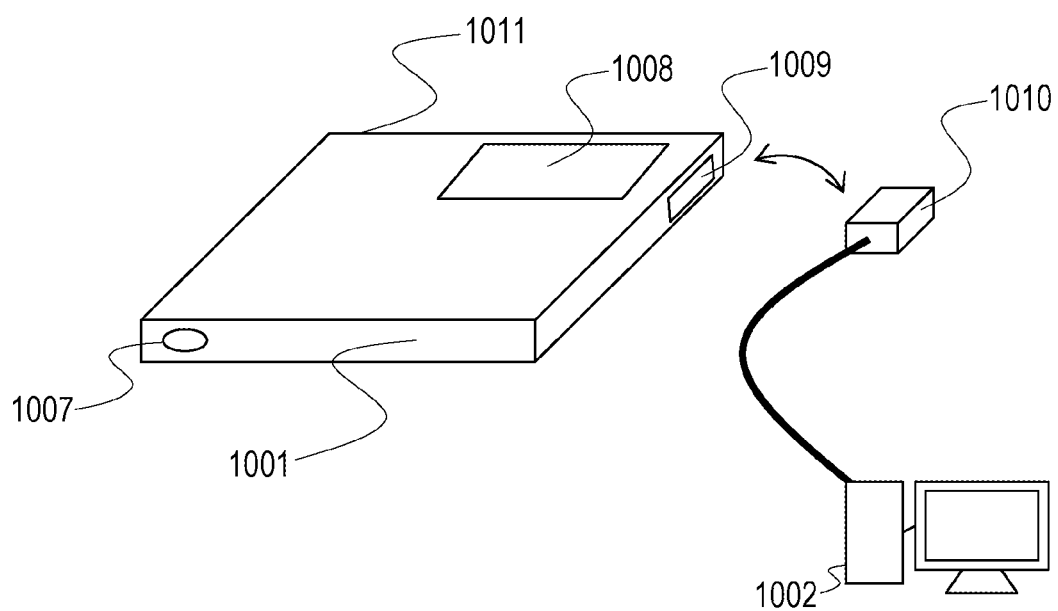
FIG. 3 is a diagram illustrating the appearance of a radiographic imaging apparatus according to the first embodiment.

FIG. 3 illustrates an exemplary appearance of the radiographic imaging apparatus 1001. The radiographic imaging apparatus 1001 includes the radiation detector (100 in FIG. 4) which detects a delivered dose of radiation emitted from the radiation source 1003. The radiographic imaging apparatus 1001 has a housing 1011. The housing 1011 houses at least the radiation detector 100 inside. For example, the radiographic imaging apparatus 1001 is a portable radiographic imaging apparatus 1001.

The radiographic imaging apparatus 1001 includes a power button 1007, a battery unit 1008, and a connector connecting unit 1009. These components are disposed on the side surfaces of the housing 1011. The power button 1007 has a function of receiving, from the outside, an operation for starting/stopping power supply to the components of the radiographic imaging apparatus 1001. As the power button 1007, for example, a pushbutton switch, a selector switch, or a touch panel may be used.

The battery unit 1008 supplies power to the components of the radiographic imaging apparatus 1001 with a predetermined voltage at which the battery is charged. The battery unit 1008 may be detached. In this case, the battery is charged by using a recharger.

The radiographic imaging apparatus 1001 is capable of communicating with the control apparatus 1002 in a wired or wireless manner. The radiographic imaging apparatus 1001 includes the connector connecting unit 1009 as a wired communication unit. The radiographic imaging apparatus 1001 may further include a cable 1010 as a wired communication unit. The radiographic imaging apparatus 1001 is capable of receiving/transmitting information from/to the control apparatus 1002 via the wired communication unit. The connector connecting unit 1009 may mechanically or electrically connect the radiographic imaging apparatus 1001 to the control apparatus 1002 by using the cable 1010.

The control apparatus 1002 may communicate with the radiographic imaging apparatus 1001 selectively through wired communication or wireless communication. When the cable 1010 connects the radiographic imaging apparatus 1001 to the control apparatus 1002, the communication path between the apparatuses is automatically switched to wired communication. The control apparatus 1002 performs the switching control. Instead of automatic switching of the communication path, the control apparatus 1002 may use an input to the input device to select one of the wired communication path and the wireless communication path through which information is obtained.

Figure 4:
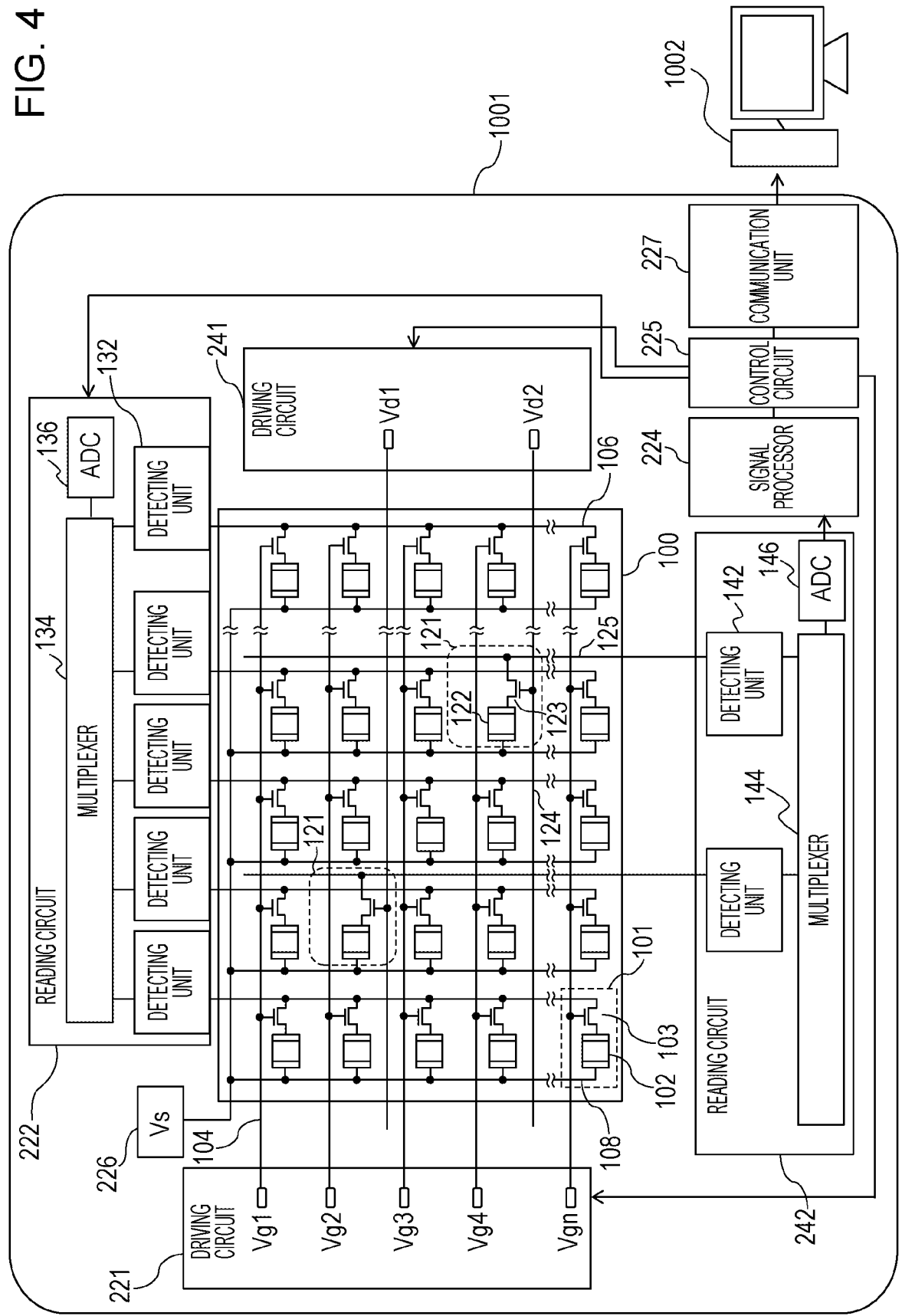
FIG. 4 is a diagram illustrating the configuration of the radiographic imaging apparatus according to the first embodiment.

FIG. 4 is a diagram illustrating the configuration of the radiographic imaging apparatus 1001 according to the first embodiment. The radiographic imaging apparatus 1001 includes the radiation detector 100. The radiation detector 100 includes multiple pixels arranged in multiple rows and multiple columns. In the description below, an area in which the pixels are arranged in the radiation detector 100 is regarded as an imaging area. The pixels include multiple imaging pixels 101 for obtaining a radiographic image and detecting pixels 121 for detecting radiation. Each of the imaging pixels 101 includes a first conversion device 102 which converts radiation into an electric signal and a first switch 103 which is disposed between a column signal line 106 and the first conversion device 102. Each of the detecting pixels 121 includes a second conversion device 122 which converts radiation into an electric signal and a second switch 123 which is disposed between a detection signal line 125 and the second conversion device 122.

Each of the first conversion device 102 and the second conversion device 122 includes a scintillator which converts radiation into light and a photoelectric conversion device which converts light into an electric signal. The scintillator is typically formed as a sheet so as to cover the imaging area, and may be shared by multiple pixels. Alternatively, each of the first conversion device 102 and the second conversion device 122 may include a conversion device which directly converts radiation into light.

Each of the first switch 103 and the second switch 123 may include, for example, a thin film transistor (TFT) in which an active region is formed of a semiconductor material, such as amorphous silicon or polycrystalline silicon (desirably polycrystalline silicon).

The radiographic imaging apparatus 1001 includes multiple column signal lines 106 and multiple drive lines 104. Each of the column signal lines 106 is provided for a corresponding one of the multiple columns in the imaging area. Each of the drive lines 104 is provided for a corresponding one of the multiple rows in the imaging area. Each of the drive lines 104 is driven by a driving circuit 221.

A first electrode of the first conversion device 102 is connected to a first main electrode of the first switch 103. A second electrode of the first conversion device 102 is connected to a bias line 108. A single bias line 108 extends in the column direction, and is connected commonly to the second electrodes of the conversion devices 102 arranged in the column direction. The bias line 108 receives a bias voltage Vs from a power supply circuit 226. The second main electrodes of the first switches 103 in the imaging pixels 101 included in a single column are connected to a single column signal line 106. The control electrodes of the first switches 103 of the imaging pixels 101 included in a single row are connected to a single drive line 104.

The column signal lines 106 are connected to a reading circuit 222. The reading circuit 222 may include multiple detecting units 132, a multiplexer 134, and an analog-digital converter (hereinafter referred to as an AD converter) 136. Each of the column signal lines 106 is connected to a corresponding one of the detecting units 132 in the reading circuit 222. A single column signal line 106 corresponds to a single detecting unit 132. The detecting unit 132 includes, for example, a differential amplifier. The multiplexer 134 selects the multiple detecting units 132 one by one in a predetermined order, and supplies a signal from the selected detecting unit 132 to the AD converter 136. The AD converter 136 converts the supplied signal into a digital signal for output.

A first electrode of the second conversion device 122 is connected to a first main electrode of the second switch 123. A second electrode of the second conversion device 122 is connected to a bias line 108. A second main electrode of the second switch 123 is electrically connected to the detection signal line 125. The control electrode of the second switch 123 is electrically connected to a drive line 124. The radiographic imaging apparatus 1001 may include multiple detection signal lines 125. A single detection signal line 125 may be connected to one or more detecting pixels 121. The drive line 124 may be driven by a driving circuit 241. A single drive line 124 may be connected to one or more detecting pixels 121.

The detection signal lines 125 are connected to a reading circuit 242. The reading circuit 242 may include multiple detecting units 142, a multiplexer 144, and an AD converter 146. Each of the detection signal lines 125 may be connected to a corresponding one of the detecting units 142 in the reading circuit 242. A single detection signal line 125 corresponds to a single detecting unit 142. The detecting unit 142 includes, for example, a differential amplifier. The multiplexer 144 selects the multiple detecting units 142 one by one in a predetermined order, and supplies a signal from the selected detecting unit 142 to the AD converter 146. The AD converter 146 converts the supplied signal into a digital signal for output. The output of the reading circuit 242 (the AD converter 146) is supplied to a signal processor 224 which processes the output. The signal processor 224 outputs information indicating irradiation of radiation emitted onto the radiographic imaging apparatus 1001, on the basis of the output of the reading circuit 242 (the AD converter 146). Specifically, for example, the signal processor 224 detects irradiation of radiation emitted onto the radiographic imaging apparatus 1001, and calculates a dose of irradiation of radiation and/or the integrated irradiation dose. The signal processor 224 determines whether or not irradiation using the radiation source 103 is to be controlled, on the basis of the delivered dose and a predetermined threshold (reference value). In the first embodiment, the signal processor 224 functions as a determining unit.

A control circuit 225 has overall control of the driving circuit 221, the reading circuit 222, the driving circuit 241, and the reading circuit 242. The control circuit 225 controls the driving circuits 221 and 241 and the reading circuits 222 and 242, on the basis of the information from the signal processor 224. For example, the control circuit 225 controls a start and an end of exposure (accumulation of charge corresponding to emitted radiation, which is performed by the imaging pixel 101), on the basis of the information from the signal processor 224.

A communication unit 227 has a function of transmitting a detection result from the radiation detector 100, to the control apparatus 1002. The communication unit 227 includes two communication units, a wired communication unit and a wireless communication unit.

The control apparatus 1002 is capable of communicating with the radiographic imaging apparatus 1001 selectively through wired communication and wireless communication. Reception/transmission of information between the radiographic imaging apparatus 1001 and the control apparatus 1002 may be performed in such a manner that the communication controller 10021 communicates with at least one of the two communication units. The difference between the communication units will be described. Communication using the wireless communication unit achieves portability of the radiographic imaging apparatus 1001 compared with wired communication. Therefore, the radiographic imaging apparatus 1001 may be used in various types of imaging, such as typical radiography, slot radiography, and mobile radiography.

In contrast, the communication speed in communication using the wireless communication unit is slower than that in wired communication. In addition, compared with wired communication, wireless communication is likely to be affected by noise or the like, and communication accuracy is unstable. A user using the radiographic imaging system 1000 may select one from the two communication units. Accordingly, the user may select radiography using dose control, in consideration of the advantages of the two communication units.

The wired communication unit includes a circuit constituting a path for information transmission, and the connector unit 1009 described above. For example, a communication standard in which predetermined arrangements are defined is used for receiving/transmitting information by using the wired communication unit. As the communication standard, for example, RS232C or USB (registered trademark) may be used. The communication standard may be another specific standard in which predetermined arrangements are defined between apparatuses.

The wireless communication unit similarly includes a circuit constituting a path for information transmission. For example, the wireless communication unit includes a circuit substrate including a communication circuit, and an antenna (not illustrated). The antenna receives/transmits wireless radio waves. For example, the wireless communication unit performs communication via the antenna using a protocol based on a wireless LAN. For the wireless communication unit, a frequency band, a standard, and a scheme in wireless communication are not particularly limited, and a scheme, for example, short range wireless communication such as Bluetooth (registered trademark) or ultra wideband (UWB), may be used. The wireless communication unit may support multiple wireless communication schemes, and one may be selected from the multiple communication schemes to perform communication.

The configuration of the radiation detector 100 is not limited to this. That is, in addition to a first radiation detector, a second radiation detector which is separately formed and which is different from the first radiation detector may be included. The second radiation detector detects a delivered dose of radiation emitted from the radiation source, and uses the delivered dose to calculate the integrated irradiation dose. Further, the second radiation detector may be disposed on the outside of the housing 1010 of the radiographic imaging apparatus 1001. The second radiation detector may be, for example, an ionization chamber.

Figure 5A:
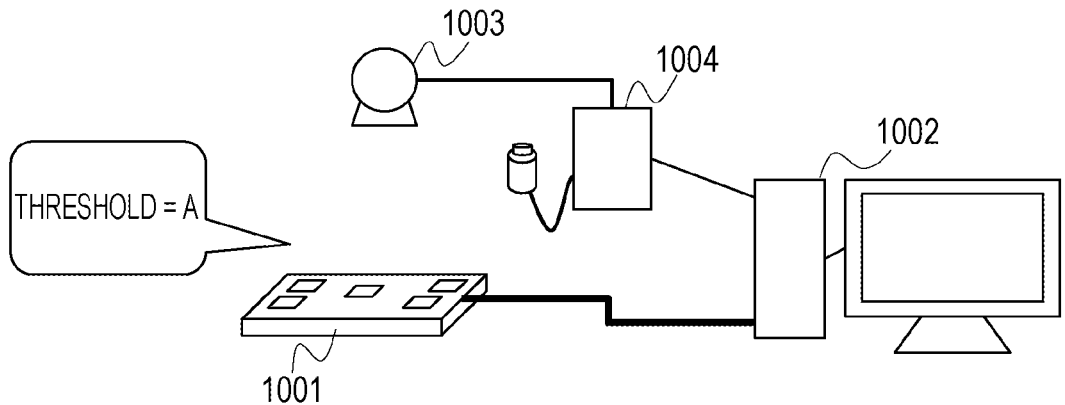
FIG. 5A is a diagram illustrating how a communication unit relates to dose control according to the first embodiment.
Figure 5B:
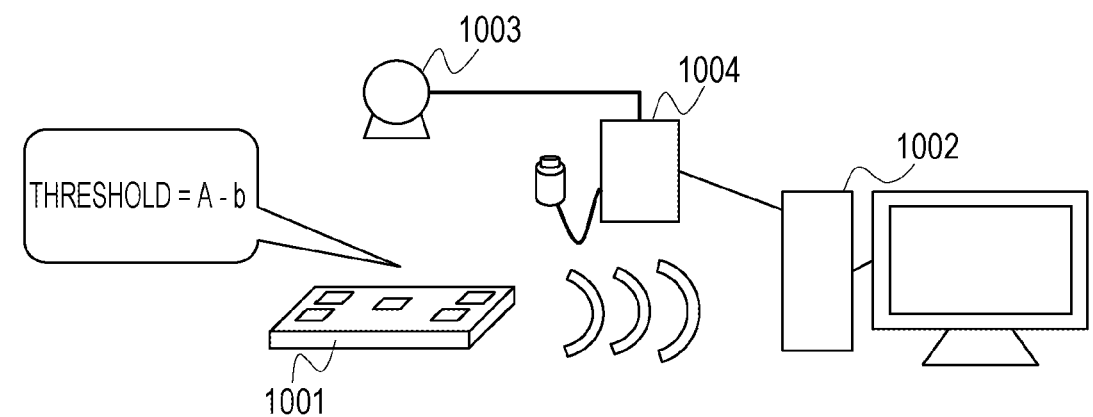
FIG. 5B is a diagram illustrating how the communication unit relates to dose control according to the first embodiment.
Figure 5C:
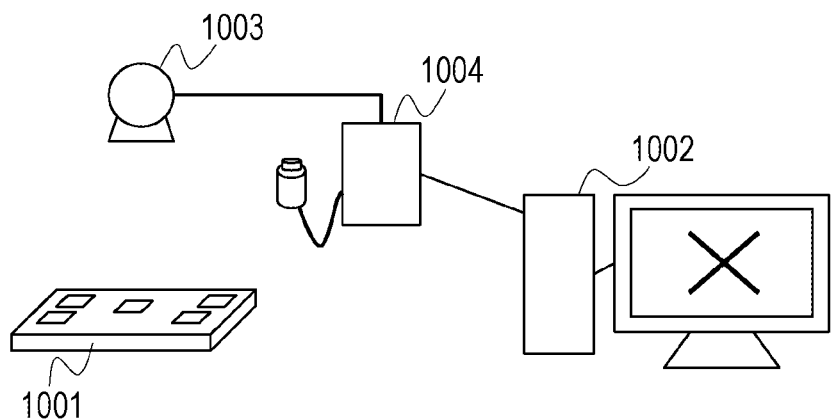
FIG. 5C is a diagram illustrating how the communication unit relates to dose control according to the first embodiment.

Referring to FIGS. 5A to 5C, dose control operations performed in the radiographic imaging system 1000 according to the first embodiment will be described. The radiographic imaging system 1000 determines a determination reference used by the determining unit, on the basis of which communication unit, the wired communication unit or the wireless communication unit, is connected to the control apparatus 1002.

In the first embodiment, as illustrated in FIGS. 5A to 5C, a threshold for dose control is changed depending on the communication unit between the communication unit 227 of the radiographic imaging apparatus 1001 and the control apparatus 1002. FIG. 5A illustrates a case in which the wired communication unit is used to perform communication between the radiographic imaging apparatus 1001 and the control apparatus 1002. FIGS. 5B and 5C illustrate a case in which the wireless communication unit is used to perform communication between the radiographic imaging apparatus 1001 and the control apparatus 1002. FIG. 5B illustrates a case in which the environment of wireless communication between the radiographic imaging apparatus 1001 and the control apparatus 1002 is good. FIG. 5C illustrates a case in which the environment of wireless communication between the communication unit 227 of the radiographic imaging apparatus 1001 and the control apparatus 1002 is not good.

In the radiographic imaging system 1000, the signal processor 224 makes a determination on the basis of the delivered dose.

In FIG. 5A, the control apparatus 1002 may substantially obtain determination results without delay, and may exert control. However, in FIGS. 5B and 5C, because of communication delay in wireless communication, the control apparatus 1002 may sometimes fail to obtain determination results without delay and exert control. Therefore, when wired communication with the control apparatus 1002 is performed, the signal processor 224 (determining unit) makes a determination on the basis of the integrated value of delivered doses. In contrast, when wireless communication with the control apparatus 1002 is performed, the signal processor 224 (determining unit) makes a determination on the basis of the integrated value of delivered doses and a communication delay time in the wireless communication with the control apparatus 1002.

In other words, the signal processor 224 (determining unit) holds thresholds for determining stopping of irradiation in automatic dose control, as different values in the radiographic imaging apparatus 1001 in accordance with whether wired communication or wireless communication is performed, on the basis of the difference in communication speed of wired communication and that in wireless communication. The signal processor 224 (determining unit) determines whether or not irradiation is to be stopped. The radiographic imaging apparatus 1001 transmits the determination result to the control apparatus 1002. The threshold in wireless communication is determined from a reaching time predicted from indicators, such as communication intensity and a communication speed.

Referring to FIG. 6, dose control performed by the signal processor 224 (determining unit) in wireless communication will be specifically described. For example, as illustrated in FIG. 6, the signal processor 224 holds a threshold, as A, for automatic dose control in wired communication performed between the communication unit 227 of the radiographic imaging apparatus 1001 and the control apparatus 1002. The signal processor 224 holds a threshold, as A-b (b is a value larger than zero), for automatic dose control in wireless communication performed between the communication unit 227 of the radiographic imaging apparatus 1001 and the control apparatus 1002.

In wired communication, when the signal processor 224 determines that the integrated value of delivered doses is smaller than the threshold A, the radiographic imaging apparatus 1001 transmits a continuous irradiation signal to the control apparatus 1002, or no signals are transmitted. When the signal processor 224 determines that the integrated value of delivered doses is equal to or larger than the threshold A, an irradiation stop signal (determination result) is transmitted to the control apparatus 1002. In response to reception of the irradiation stop signal, the control apparatus 1002 stops irradiation using the radiation source 1003, through the radiation generating apparatus 1004. At that time, the radiographic imaging apparatus 1001 may simultaneously transmit the integrated value of delivered doses or the like to the control apparatus 1002.

In contrast, in wireless communication, a transmission delay time is predicted in the control apparatus 1002 from the communication rate between the radiographic imaging apparatus 1001 and the control apparatus 1002, and, for example, a predicted delay time of a (us) is output to the radiographic imaging apparatus 1001. The communication rate between the radiographic imaging apparatus 1001 and the control apparatus 1002 may be changed in accordance with the environment in which the radiographic imaging system 1000 is installed, or the like.

When the communication rate decreases, a delay time increased. Even when the radiographic imaging apparatus 1001 transmits an irradiation stop signal, the transmission may take time. Therefore, in consideration of a predicted delay time of a (us), the signal processor 224 sets the threshold in wireless communication to A-b which is smaller than the threshold in wired communication. The signal processor 224 predicts the transmission delay, and makes the actual integrated dose smaller than the threshold in wired communication. Accordingly, the control apparatus 1002 may stop irradiation of radiation at an adequate timing. In other words, in wired communication, when the actual integrated dose reaches an adequate dose for a subject, the signal processor 224 may output a determination result. In contrast, in wireless communication, the signal processor 224 may output a determination result at a timing before the actual dose reaches an adequate dose for a subject.

At that time, the radiographic imaging apparatus 1001 may hold in advance a table of delay times corresponding to communication rates, inside the control apparatus 1002. For example, when the communication rate is 100 Mbps, a delay of 100 us is predicted. The control apparatus 1002 transmits the delay time as a (us) to the radiographic imaging apparatus 1001. The radiographic imaging apparatus 1001 may hold the data table of delay times, and may use the table in calculation of the threshold.

The radiographic imaging apparatus 1001 determines that irradiation is to be stopped, and transmits an irradiation stop signal. Alternatively, the control apparatus 1002 may have the determining unit and execute the operations. Instead, the control apparatus 1002 may exert control so that automatic dose control performed by the radiographic imaging apparatus 1001 is inhibited in wireless communication. As illustrated in FIG. 5C, the control apparatus 1002 exerts control so that a message that automatic dose control is inhibited is displayed on a display device on the control apparatus 1002 in a recognizable manner. A specific description will be made. For example, occurrence of a state in which a received signal strength indication (RSSI) indicating the intensity of a wireless communication signal is, for example, equal to or smaller than −80 dBm, or in which a signal-to-noise ratio (SNR) is equal to or smaller than 20 dB is used as an indicator. In this case, when at least one of an RSSI and an SNR is less than a threshold, the control apparatus 1002 determines that this is a period in which the wireless communication environment is bad. The control apparatus 1002 may inhibit automatic dose control of the radiographic imaging apparatus 1001 on the basis of the determination result. Instead of inhibition, the control apparatus 1002 may exert control so that a message to prompt switching to the wired communication unit is displayed on the display device on the control apparatus 1002.

The control apparatus 1002 may change a setting for switching between wired communication and wireless communication which are performed between the radiographic imaging apparatus 1001 and the control apparatus 1002, in accordance with whether or not the cable 1010 is attached. For example, when the cable 1010 is connected to the control apparatus 1002, wired communication is performed. When the cable 1010 is not connected to the control apparatus 1002 (when detached), control is exerted so that switching to wireless communication is performed. Regardless of whether or not the cable 1010 is attached, the control apparatus 1002 may cause a user to select a communication unit by using the input device. The control apparatus 1002 determines which type of communication is to be performed, and a communication unit of the determined type is used at once. Accordingly, the communication unit is available at once without a resetting operation performed by a user. For example, even when a wired cable is connected, a situation may occur in which wireless communication is to be performed. In consideration of this, a user may perform a selecting operation.

As described above, the radiography system according to the first embodiment may provide an advantageous technique for adequately obtaining an irradiation dose of radiation in accordance with a communication path.

Second Embodiment

Figure 7:
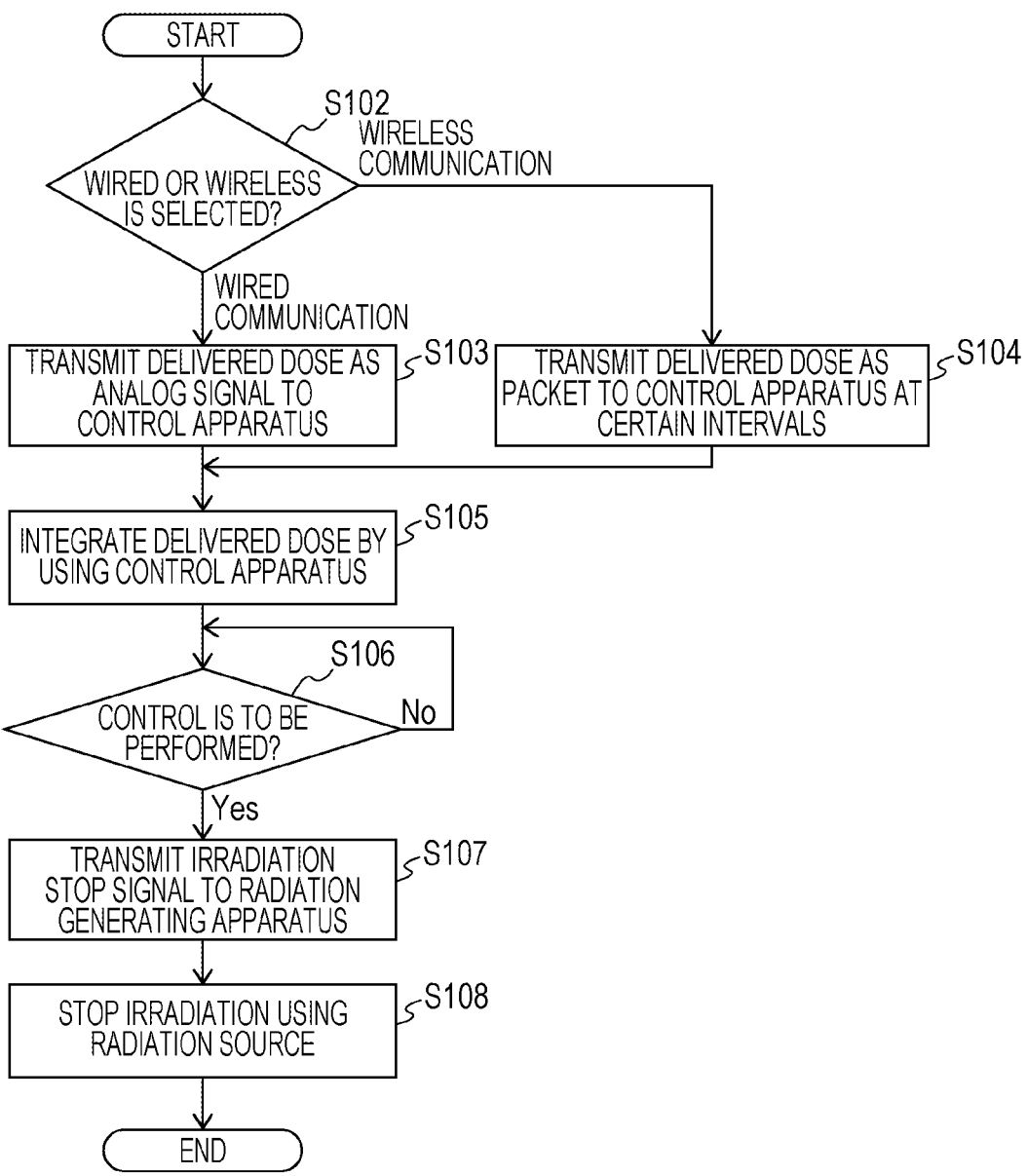
FIG. 7 is a flowchart for dose control according to a second embodiment.

Referring to FIG. 7, a second embodiment will be described. The second embodiment is different from the first embodiment in that information transmitted from the radiographic imaging apparatus 1001 is changed on the basis of whether or not which communication unit, the wired communication unit or the wireless communication unit, is connected to the control apparatus 1002. In addition, the second embodiment is different from the first embodiment in that the control apparatus 1002 makes a determination on the basis of the detection result from the radiation detector 100. That is, in the second embodiment, the control apparatus 1002 functions as a determining unit. FIG. 7 is a flowchart illustrating dose control performed in the second embodiment. In the description below, a specific description will be made by using the flowchart.

In S102, the control apparatus 1002 determines which, wired communication or wireless communication, is to be performed to communicate with the radiographic imaging apparatus 1001.

A case in which the control apparatus 1002 communicates with the communication unit 227 of the radiographic imaging apparatus 1001 through wired communication will be described. In S103, the communication unit 227 transmits, to the control apparatus 1002, a delivered dose detected by the signal processor 224.

In S105, the control apparatus 1002 calculates the integrated value of delivered doses. In S106, the control apparatus 1002 compares the integrated value with the threshold. If the control apparatus 1002 determines that the integrated value is equal to or larger than the threshold, the control apparatus 1002 transmits an irradiation stop signal to the radiation generating apparatus 1004 in S107. On the basis of the irradiation stop signal, the radiation generating apparatus 1004 stops irradiation of radiation emitted from the radiation source 1003 in S108.

The communication unit 227 desirably outputs a delivered dose as an analog signal when wired communication is performed. In this case, analog-digital conversion is not necessary, achieving faster processing. In addition, outputting of a delivered dose as an analog signal enables commonality between the connection interface (IF) of the control apparatus 1002 and the IF of an ionization chamber to be achieved, resulting in simplification of a configuration of the control apparatus 1002.

A case in which the control apparatus 1002 communicates with the radiographic imaging apparatus 1001 through wireless communication will be described. In S104, the signal processor 224 transmits, as a packet to the control apparatus 1002, both of a delivered dose detected by the radiation detector 100 and information about time at which the delivered dose is detected, at certain intervals. The control apparatus 1002 obtains the delivered dose and the time information. For example, even when a packet fails to be transferred due to the environment or the like of the wireless communication, the control apparatus 1002 may estimate information which has failed to be transferred, on the basis of the other packets, and may estimate the integrated dose. Therefore, the control apparatus 1002 may predict the time at which the integrated value of delivered doses reaches the threshold, and may determine stopping of irradiation. The processes after S107 are the same as those performed when wired communication is performed. The control apparatus 1002 desirably does not return a response (ACK) which indicates whether or not the delivered dose and the information about time at which the delivered dose is obtained are successfully received. Even when certain packet information fails to be obtained, the control apparatus 1002 may estimate the information from other delivered doses. Thus, the estimation without retransmission achieves faster processing.

As described above, in the second embodiment, significant data or signals produced from the difference between communication methods may be used to perform dose control. Therefore, even in the case where a delay time occurs in a communication path or where transmission fails, excessive irradiation may be suppressed, and radiography with a low dose may be achieved. In the second embodiment, the control apparatus 1002 determines whether or not irradiation of radiation is to be stopped, on the basis of the integrated value of delivered doses. Therefore, even when an ionization chamber is used, commonality between the IF of the imaging system and that of the control apparatus may be achieved. Accordingly, a reduction in installation cost of the system is achieved, which is useful for a user.

Third Embodiment

Figure 8:
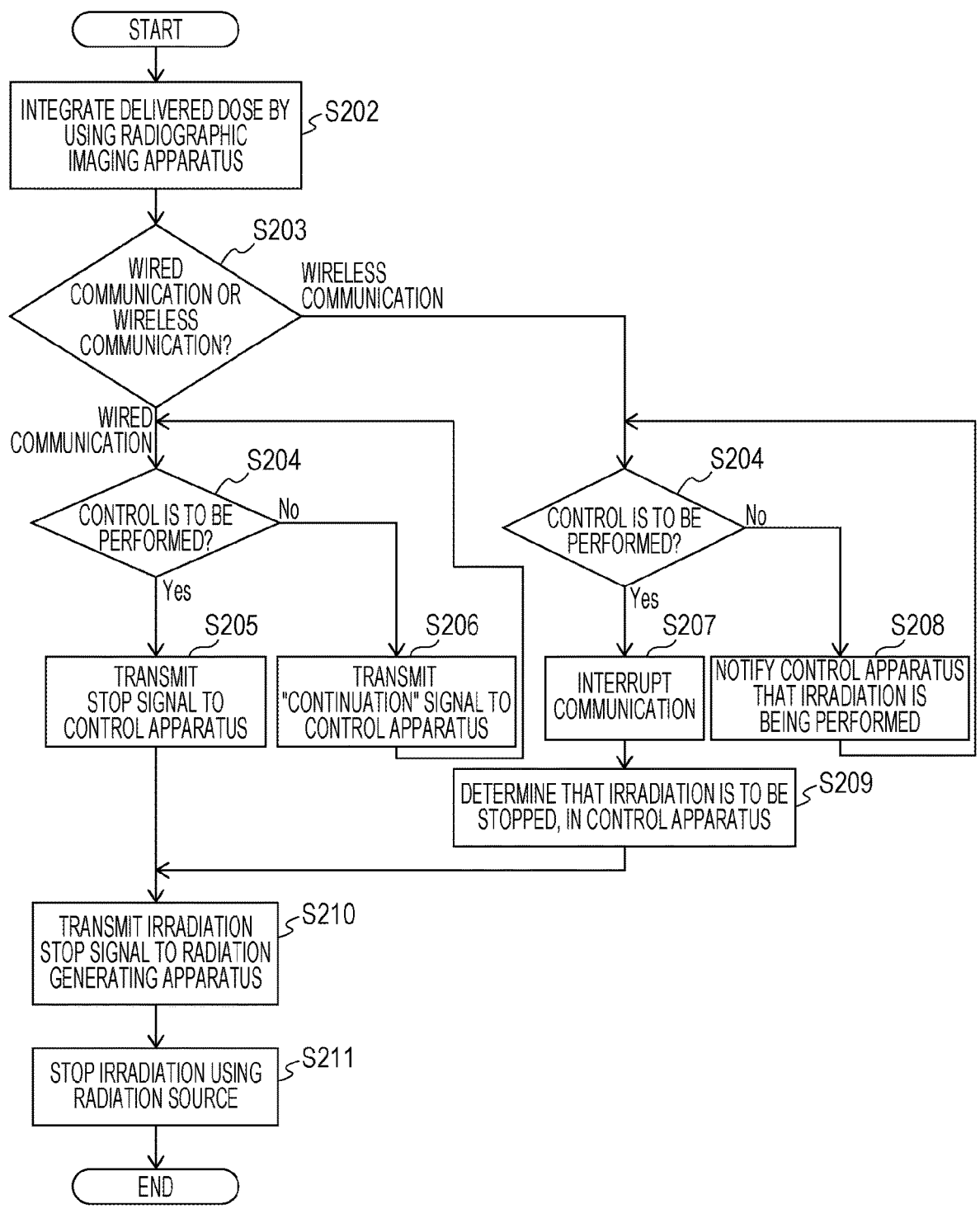
FIG. 8 is a flowchart for dose control according to a third embodiment.

Referring to FIG. 8, a third embodiment will be described. In the third embodiment, the way in which a determination result is transmitted from the communication unit 227 is changed in accordance with the communication unit used between the communication unit 227 of the radiographic imaging apparatus 1001 and the control apparatus 1002. FIG. 8 is a flowchart of dose control according to the third embodiment. In the description below, a specific description will be made by using the flowchart.

In S202, the signal processor 224 calculates the integrated value of delivered doses on the basis of the delivered doses. In S203, the control circuit 225 determines whether which connection, a wired communication connection or a wireless communication connection, has been established with the control apparatus 1002. The determination may be made by the control apparatus 1002. In S204, the signal processor 224 determines whether the integrated value of delivered doses reaches the threshold. In S203, the signal processor 224 changes the way in which the determination result is transmitted, on the basis of which connection, a wired communication connection or a wireless communication connection, has been established with the control apparatus 1002. In the description below, the difference between the ways in which a determination result is transmitted will be described.

A case in which a connection has been established through wired communication will be described. In S204, if the integrated value of delivered doses is smaller than the predetermined threshold, the control circuit 225 performs the process in S206. If the integrated value of delivered doses is equal to or larger than the predetermined threshold, the control circuit 225 performs the process in S205.

In S206, the control circuit 225 constantly transmits a continuation signal to the control apparatus 1002. In contrast, in S205, the control circuit 225 transmits a stop signal to the control apparatus 1002. That is, the control circuit 225 transmits a binary signal indicating a determination result.

In S210, the control apparatus 1002 transmits an irradiation stop signal to the radiation generating apparatus 1004 in accordance with the determination result, and stops irradiation of radiation emitted from the radiation source 1003. When a wired connection has been established, the communication speed is faster than that in wireless communication. Therefore, after the determination process in S204, signal generation followed by transmission of the stop signal is desirable as dose control because this is more reliable.

A case in which a wireless communication connection has been established will be described. In S204, if the integrated value of delivered doses is smaller than the predetermined threshold, the control circuit 225 performs the process in S208. If the integrated value of delivered doses is equal to or larger than the predetermined threshold, the control circuit 225 performs the process in S207.

In S208, the control circuit 225 continues to transmit, to the control apparatus 1002, a signal (hereinafter referred to as an irradiation signal) indicating that irradiation is being performed. In this case, the wireless communication scheme is one using a radio wave, a sound, light, or the like.

In S207, the control circuit 225 interrupts communication (transmission) with the control apparatus 1002. In S209, the control apparatus 1002 determines that the wireless communication has been interrupted. When the wireless communication has been interrupted, the control apparatus 1002 determines that the integrated value exceeds the threshold and that this is a notification indicating the end of irradiation. In wireless communication, unlike the operation in wired communication, communication is interrupted in S207 without generating a stop signal after the determination process. Therefore, the control apparatus 1002 does not need to perform a process of determining whether or not information transmitted through wireless communication is an "irradiation stop signal", achieving a quicker response in response control. In addition, even when an "irradiation stop signal" fails to be received due to communication failure or the like, the control apparatus 1002 may stop irradiation. The control apparatus 1002 stops irradiation in response to interruption in reception of an irradiation signal, achieving suppression of excessive exposure on a subject which is made due to communication failure.

Similarly to the case in which wired communication is performed, the control apparatus 1002 performs the processes in S210 and S211, and stops irradiation using the radiation source 1003.

For both of the wired communication unit and the wireless communication unit, integration of delivered doses and threshold determination for the integrated value are performed in the radiographic imaging apparatus 1001, and a signal indicating an irradiation stop signal or a continuous irradiation signal is transmitted to the control apparatus 1002. Therefore, the processing time in the control apparatus 1002 is decreased, achieving a quicker response in stop control.

As described above, in the third embodiment, the integrated value of delivered doses is compared with a threshold in the radiographic imaging system, achieving real-time control. In particular, when the radiographic imaging apparatus is connected to the control apparatus through wireless communication, transmission data to the control apparatus is simplified, achieving a quicker response in automatic dose control and a lower dose of irradiation.

Fourth Embodiment

Figure 9A:
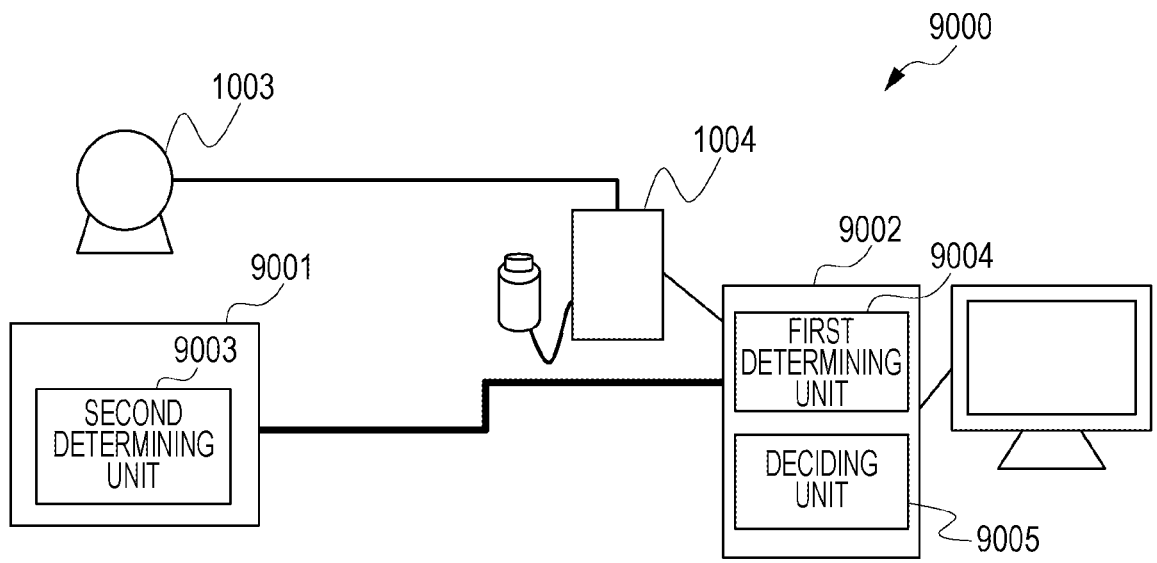
FIG. 9A is a diagram illustrating a radiographic imaging system according to a fourth embodiment.
Figure 9B:
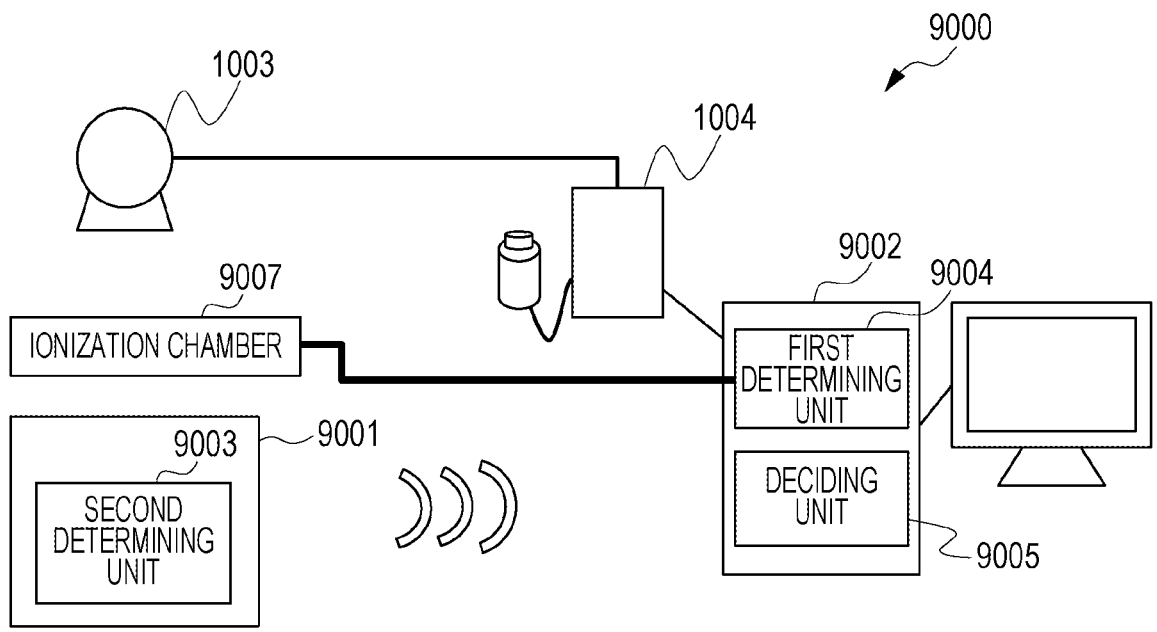
FIG. 9B is a diagram illustrating a radiographic imaging system according to the fourth embodiment.

Referring to FIGS. 9A and 9B, a fourth embodiment will be described. In the fourth embodiment, through communication between the communication unit 227 of a radiographic imaging apparatus 9001 and a control apparatus 9002, it is determined which, the radiographic imaging apparatus 9001 or the control apparatus 9002, is to control irradiation using the radiation source. In other words, the control apparatus 9002 determines which, a delivered dose or a determination result, is to be obtained from the radiation detector. Components which are not specifically described have configurations similar to those in the first embodiment.

FIG. 9A is a diagram illustrating a radiographic imaging system constructed in the case where the radiographic imaging apparatus 9001 communicates with the control apparatus 9002 through wired communication, according to the fourth embodiment. FIG. 9B is a diagram illustrating a radiographic imaging system constructed in the case where the radiographic imaging apparatus 9001 communicates with the control apparatus 9002 through wireless communication, according to the fourth embodiment.

A radiographic imaging system 9000 includes the radiographic imaging apparatus 9001, the control apparatus 9002, the radiation source 1003, and the radiation generating apparatus 1004.

The radiographic imaging apparatus 9001 includes a second determining unit 9003. The control apparatus 9002 includes a first determining unit 9004 and a deciding unit 9005.

The deciding unit 9005 switches a unit that is to make a determination, depending on the communication unit used between the communication unit 227 of the radiographic imaging apparatus 9001 and the control apparatus 9002. Specifically, the deciding unit 9005 determines whether the determination process of comparing the integrated value of delivered doses with a threshold is to be performed by the first determining unit 9004 or the second determining unit 9003.

When the communication unit 227 of the radiographic imaging apparatus 9001 is connected to the control apparatus 9002 through wired communication, the deciding unit 9005 causes the first determining unit 9004 to perform the determination process. In this case, the radiographic imaging apparatus 9001 transmits a delivered dose to the control apparatus 9002. The first determining unit 9004 integrates obtained delivered doses, determines whether or not irradiation is to be stopped, and transmits a stop signal to the radiation generating apparatus 1004.

In contrast, when the communication unit 227 of the radiographic imaging apparatus 9001 is connected to the control apparatus 9002 through wireless communication, the deciding unit 9005 causes the second determining unit 9003 to perform the determination process. In this case, the second determining unit 9003 calculates the integrated value of delivered doses, and determines whether or not the integrated value reaches the threshold. The radiographic imaging apparatus 9001 transmits the determination result to the control apparatus 9002. The control apparatus 9002 transmits an irradiation stop signal to the radiation generating apparatus 1004 on the basis of the determination result.

The radiographic imaging system 9000 may capture an image by using an ionization chamber 9007 as a device that is used to detect a delivered dose and that is separate from the radiographic imaging apparatus 9001. The ionization chamber 9007 connected to the control apparatus 9002 only through wired communication does not perform the determination process, and outputs a signal on the basis of a delivered dose. Therefore, in the case where the ionization chamber 9007 is used in capturing of an image, the control apparatus 9002 may determine whether or not irradiation is to be stopped. Therefore, even in the case where either of the radiographic imaging apparatus 9001 and the ionization chamber 9007 is used to perform dose control, when the control apparatus 9002 is connected to the radiographic imaging apparatus 9001 through wired communication, the same connection IF as that of the ionization chamber 9007 may be used.

As described above, in the fourth embodiment, even in a system having an ionization chamber, a low dose of irradiation may be achieved in wired communication and wireless communication. A user may use control methods which are suitable for operations and in which reliability of communication using a wired communication unit and portability of a wireless communication unit are achieved.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD) (trademark)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-232522, filed Nov. 28, 2015, which is hereby incorporated by reference herein in its entirety.

The invention claimed is:
1. A radiographic imaging system comprising:
a radiation detector that detects radiation emitted from a radiation source;

a controller that is capable of selectively performing wired communication or wireless communication with the radiation detector and that controls the radiation source; and a determining unit that determines whether or not a delivered dose delivered to the radiation detector reaches a reference value, by using a predetermined determination method on the basis of the detection result from the radiation detector, wherein the controller controls the radiation source on the basis of the determination result from the determining unit, and the determining unit switches the predetermined determination method in accordance with whether the selected communication is the wireless communication or the wired communication.

2. The radiographic imaging system according to claim 1, wherein the controller makes a selection in such a manner that, when the radiation detector is connected to a cable, the wired communication is to be performed, and, when the radiation detector is not connected to the cable, wireless communication is to be performed.

3. The radiographic imaging system according to claim 1, further comprising:

a radiographic imaging apparatus that includes the radiation detector inside, wherein the radiographic imaging apparatus includes the determining unit.

4. The radiographic imaging system according to claim 3, wherein the determining unit changes the predetermined determination method on the basis of which communication, the wired communication or the wireless communication, has been selected.

5. The radiographic imaging system according to claim 4, wherein, when the wired communication has been selected, the determining unit makes the determination on the basis of an integrated value of delivered doses, and, when the wireless communication has been selected, the determining unit makes the determination on the basis of the integrated value of delivered doses and a communication delay time in the wireless communication.

6. The radiographic imaging system according to claim 5, wherein the controller exerts control in such a manner that the wireless communication is inhibited when an environment in the wireless communication is unfavorable, and that a message about the inhibition is provided as a notification in a recognizable manner.

7. The radiographic imaging system according to claim 1, wherein the controller includes the determining unit.

8. The radiographic imaging system according to claim 7, wherein the determining unit changes the predetermined determination method on the basis of which communication, the wired communication or the wireless communication, has been selected.

9. The radiographic imaging system according to claim 8, wherein, when the wired communication has been selected, the determining unit makes the determination on the basis of an integrated value of delivered doses, and, when the wireless communication has been selected, the determining unit makes the determination on the basis of the integrated value of delivered doses and a time at which the radiation detector measures the radiation.

10. The radiographic imaging system according to claim 1, wherein, in the case where the wireless communication has been selected, when a received signal is stopped, the controller determines that the radiation source is to be controlled, the received signal being received during a period in which irradiation of radiation emitted to the radiation detector continues.

11. The radiographic imaging system according to claim 3, wherein the radiographic imaging apparatus includes a housing, and wherein the housing houses the radiation detector inside.

12. The radiographic imaging system according to claim 11, wherein the radiation detector includes imaging pixels for obtaining a radiographic image and detecting pixels for obtaining the delivered dose.

13. The radiographic imaging system according to claim 1, further comprising:

an ionization chamber that detects radiation emitted from the radiation source, wherein the controller is capable of performing the wired communication with the ionization chamber, and controls the radiation on the basis of the radiation detected by the ionization chamber.

14. A control apparatus that is capable of selectively performing wired communication or wireless communication with a radiation detector detecting radiation emitted from a radiation source, and that controls the radiation detector and the radiation source, the control apparatus comprising:

a determining unit that determines whether or not a delivered dose delivered to the radiation detector reaches a reference value, by using a predetermined determination method on the basis of the detection result from the radiation detector, wherein the control apparatus controls the radiation source on the basis of the determination result from the determining unit, and the determining unit switches the predetermined determination method in accordance with whether the selected communication is the wireless communication or the wired communication.

15. A method of controlling a radiographic imaging system including a radiation detector and a controller, the radiation detector detecting radiation emitted from a radiation source, the controller being capable of selectively performing wired communication or wireless communication with the radiation detector and controlling the radiation detector and the radiation source, the method comprising:

determining whether or not a delivered dose delivered to the radiation detector reaches a reference value, by using a predetermined determination method on the basis of the detection result from the radiation detector;

switching the predetermined determination method in accordance with whether the selected communication is the wireless communication or the wired communication; and controlling the radiation source on the basis of the determination result obtained in the determining.

* * * * *